United States Patent
Yoshihara et al.

(10) Patent No.: US 12,306,194 B2
(45) Date of Patent: May 20, 2025

(54) REAGENT FOR FLUORESCENCE IMAGING OF LIPID DROPLETS IN CELL AND TISSUE

(71) Applicant: NATIONAL UNIVERSITY CORPORATION GUNMA UNIVERSITY, Gunma (JP)

(72) Inventors: Toshitada Yoshihara, Gunma (JP); Ryo Maruyama, Gunma (JP); Seiji Tobita, Gunma (JP)

(73) Assignee: NATIONAL UNIVERSITY CORPORATION GUNMA UNIVERSITY, Gunma (JP)

( * ) Notice: Subject to any disclaimer, the term of this patent is extended or adjusted under 35 U.S.C. 154(b) by 879 days.

(21) Appl. No.: 17/440,413

(22) PCT Filed: Mar. 18, 2020

(86) PCT No.: PCT/JP2020/012002
§ 371 (c)(1),
(2) Date: Sep. 17, 2021

(87) PCT Pub. No.: WO2020/189721
PCT Pub. Date: Sep. 24, 2020

(65) Prior Publication Data
US 2022/0163545 A1   May 26, 2022

(30) Foreign Application Priority Data
Mar. 19, 2019 (JP) ................. 2019-051368

(51) Int. Cl.
*C07D 519/00* (2006.01)
*G01N 21/64* (2006.01)
*G01N 33/92* (2006.01)

(52) U.S. Cl.
CPC ......... *G01N 33/92* (2013.01); *C07D 519/00* (2013.01); *G01N 21/6428* (2013.01); *G01N 2021/6439* (2013.01)

(58) Field of Classification Search
CPC ................ C07D 519/00; G01N 33/92
See application file for complete search history.

(56) References Cited

U.S. PATENT DOCUMENTS

| | | |
|---|---|---|
| 2007/0200096 A1 | 8/2007 | Kathirgamanathan et al. |
| 2007/0254183 A1 | 11/2007 | Kathirgamanathan |
| 2010/0038632 A1 | 2/2010 | Ganeshamurugan et al. |

FOREIGN PATENT DOCUMENTS

| | | |
|---|---|---|
| GB | 2 440 367 | 1/2008 |
| JP | 2009-545155 | 12/2009 |
| JP | 6241014 | 12/2017 |
| JP | 2018-145422 | 9/2018 |
| WO | 2014/142320 | 9/2014 |

OTHER PUBLICATIONS

International Search Report (ISR) issued Jun. 16, 2020 in International (PCT) Application No. PCT/JP2020/012002.

*Primary Examiner* — Shawquia Jackson
(74) *Attorney, Agent, or Firm* — Wenderoth, Lind & Ponack, L.L.P.

(57) ABSTRACT

The present invention aims to provide a fluorescent reagent capable of highly sensitive imaging of a lipid droplet at a level ranging from cultured cells to individuals. A lipid droplet detection reagent including a compound represented by the following General Formula (I) is provided.

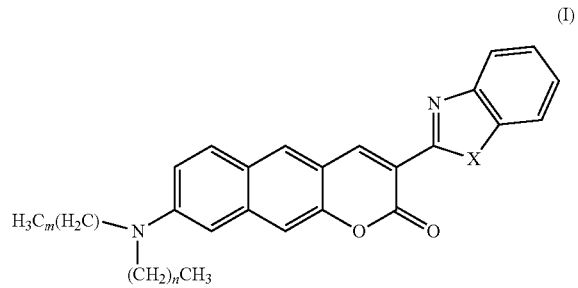

In the formula, m represents an integer of 0 to 5; n represents an integer of 0 to 5; X is selected from the group consisting of a sulfur atom, an oxygen atom, and a group represented by NR; R is a hydrogen atom or a group represented by $-(CH_2)_y CH_3$; and y represents an integer of 0 to 5.

10 Claims, 12 Drawing Sheets

BODIPY493/503

Nile Red

LipiDye

Lipi-Blue

Lipi-Green

Lipi-Red

MNs-NB

X: O (PC6O)
S (PC6S)
NH (PC6NH)
NMe (PC6NMe)

REAGENT FOR FLUORESCENCE IMAGING OF LIPID DROPLETS IN CELL AND TISSUE

TECHNICAL FIELD

The present invention relates to a fluorescence imaging reagent for lipid droplets in cells and tissues.

BACKGROUND ART

A lipid droplet (fat droplet) is a spherical organelle containing a neutral lipid such as triacylglycerol, cholesterol ester, or the like surrounded with a monolayer phospholipid membrane. Although lipid droplets are found in a large amount mainly in adipocytes, they are ubiquitously present in any cells. Although the major role of lipid droplets has been thought to be storage of neutral lipid, a recent study showed that they are involved in regulation of intracellular lipid metabolism. Besides, there is, for example, a study reporting about lipid droplets and autophagy. Thus, research on the mechanisms of the formation, growth, and degradation of lipid droplets is in progress. On the other hand, excessive accumulation of fat in a tissue (individual) leads to dysfunction of the tissue, causing development of diabetes, arteriosclerosis, and the like. Further, in recent years, there are increasing cases of development of non-alcoholic steatohepatitis (NASH), which is a type of hepatitis. If NASH is left untreated, it may lead to liver cirrhosis or liver cancer. Therefore, elucidation of the mechanisms of the formation, growth, and degradation of lipid droplets in cells and tissues is important not only for cell biology, but also for diagnosis and treatment of these diseases. Thus, development of a molecular probe for highly sensitive real-time imaging of lipid droplets in living cells and tissues is required.

Fluorescence imaging is a method that simply enables imaging of living cells and tissues, and widely used in biological and medical studies. In the academic level, a number of fluorescent reagents for imaging of lipid droplets have been reported. However, only several kinds of reagents have been practically applied. FIG. 1 shows lipid droplet fluorescence imaging reagents that are commercially available at present. BODIPY493/503 and Nile Red are used by many researchers. BODIPY493/503 shows a green fluorescence at about 500 nm, and is highly selective for lipid droplets. However, they have problems such as poor photostability, a low lipid droplet retention property, and leakage of excitation light due to a small Stokes shift (energy difference between the maximum absorption wavelength and the maximum fluorescence wavelength). Further, Nile red has low selectivity for lipid droplets since it shows abundant distribution also in organelles other than lipid droplets. Moreover, since its absorption and fluorescence spectra largely vary depending on the surrounding microenvironment, multistaining with other fluorescent reagents is difficult. Patent Document 1 reports an oil droplet-staining agent using a condensed thiophene compound. However, since the compound has peaks of excitation light widely ranging from blue to green, overlapped images make multicolor imaging difficult. In order to solve the problems, LipiDye and Lipi series (Lipi-Blue, Lipi-Green, and Lipi-Red) were developed. Although these reagents are capable of selective imaging of intracellular lipid droplets, there is no knowledge about lipid droplet imaging in a living tissue.

Regarding lipid droplet imaging in a living tissue, a nitrobenzene-substituted Nile Blue derivative (MNs-NB, FIG. 2) has been reported in Patent Document 2. In MNs-NB, a photo-induced electron transfer reaction occurs between the nitrobenzene unit and Nile blue in a polar solvent. On the other hand, in a low-polarity solvent, the photo-induced electron transfer reaction is less likely to occur, resulting in a red fluorescence. Although MNs-NB is a reagent capable of imaging of lipid droplets in a tissue, there are problems such as a low fluorescence quantum yield (0.21; in chloroform) and a small Stokes shift.

PRIOR ART DOCUMENTS

Patent Documents

[Patent Document 1] JP 2018-145422 A
[Patent Document 2] JP 6241014 B

SUMMARY OF THE INVENTION

Problems to be Solved by the Invention

As described above, fluorescent reagents for lipid droplet imaging commercially available at present are limited to those for cultured cells. Moreover, MNs-NB, which is a commercially unavailable compound, has many problems to be solved before its practical application. In view of this, an object of the present invention is to provide a fluorescent reagent capable of highly sensitive imaging of lipid droplets at a level ranging from cultured cells to individuals. Such a fluorescent reagent may significantly contribute to development of diagnostic agents and therapeutic agents for diseases caused by excessive lipid accumulation.

Means for Solving the Problems

As a result of intensive study to solve the above problems, the present inventors developed a reagent containing a coumarin skeleton, and discovered that use of this reagent enables selective fluorescence imaging of lipid droplets in cells and tissues, thereby completing the present invention More specifically, the present invention can be summarized as follows.

[1] A lipid droplet detection reagent comprising a compound represented by the following General Formula (I):

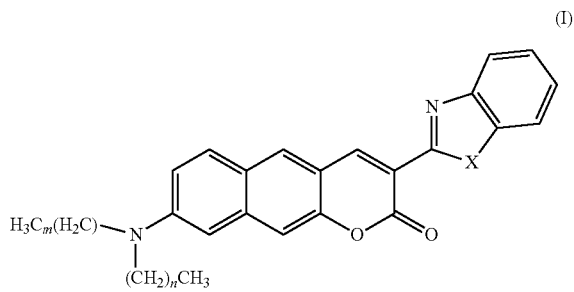

wherein
  m represents an integer of 0 to 5;
  n represents an integer of 0 to 5;
  X is selected from the group consisting of a sulfur atom, an oxygen atom, and a group represented by NR;
  R is a hydrogen atom or a group represented by —(CH$_2$)$_y$CH$_3$; and
  y represents an integer of 0 to 5.
[2] The detection reagent according to [1], wherein m and n are 1.

[3] The detection reagent according to [1] or [2], wherein y is 0.

[4] The detection reagent according to any one of [1] to [3], for detection of a lipid droplet(s) in a biological sample.

[5] The detection reagent according to [4], wherein the biological sample is a cell or a tissue.

[6] The detection reagent according to any one of [1] to [3], for detection of a lipid droplet(s) in a biological individual.

[7] A lipid droplet detection method comprising the step of:
administering the detection reagent according to any one of [1] to [6] to a biological sample or a biological individual (other than a human).

[8] The lipid droplet detection method according to [7], wherein a solution containing: a detection reagent; and a solubilizer; is administered to a biological sample or a biological individual (other than a human).

[9] The lipid droplet detection method according to [8], wherein the solubilizer is albumin.

[10] A compound represented by the following General Formula (I)':

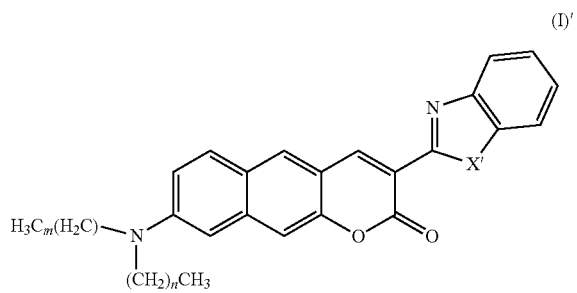

wherein
m represents an integer of 0 to 5;
n represents an integer of 0 to 5;
X' is selected from the group consisting of an oxygen atom and a group represented by NR';
R' is a group represented by —(CH$_2$)$_y$CH$_3$; and
y represents an integer of 0 to 5.

[11] The compound according to [10], wherein m and n are 1.

[12] The compound according to [10] or [11], wherein y is 0.

Advantageous Effects of the Invention

According to the present invention, a reagent capable of selective fluorescence imaging of lipid droplets in a cell or a tissue can be provided.

EMBODIMENTS FOR CARRYING OUT THE INVENTION

Figure 1:
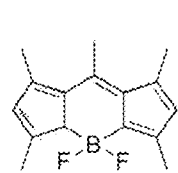
FIG. 1 shows the structural formulae of commercially available lipid droplet fluorescence imaging reagents.
Figure 1:
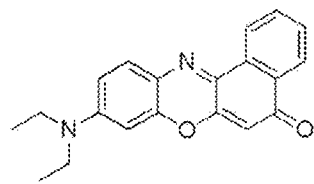
Figure 1:
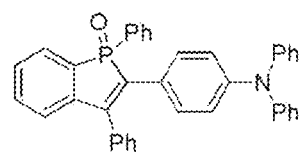
Figure 1:
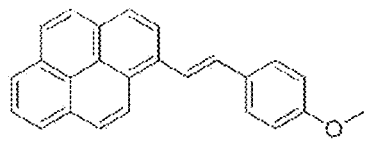
Figure 1:
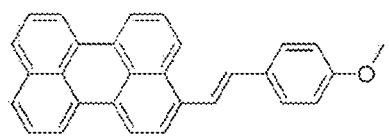
Figure 1:
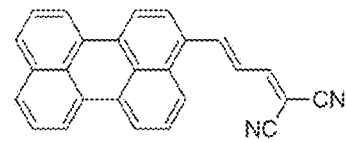
Figure 2:
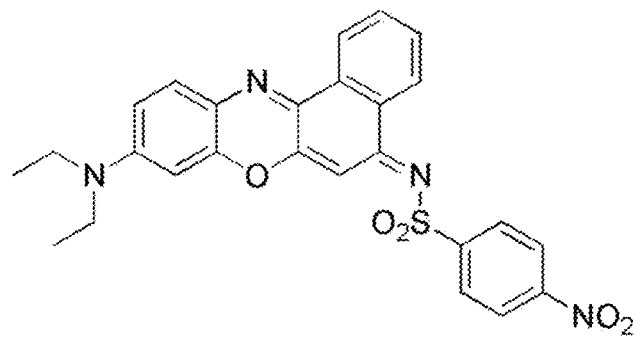
FIG. 2 shows the structural formula of a Nile Blue derivative (MNs-NB).

The present invention is described below.

<Lipid Droplet Detection Reagent>

One aspect of the present invention relates to a lipid droplet detection reagent (which may be hereinafter referred to as "lipid droplet detection reagent of the present invention") containing a compound represented by the following General Formula (I). The lipid droplet herein means a spherical droplet containing lipid, which droplet is contained in, for example, a cell.

The compound represented by the General Formula (I) is a compound having the following structure.

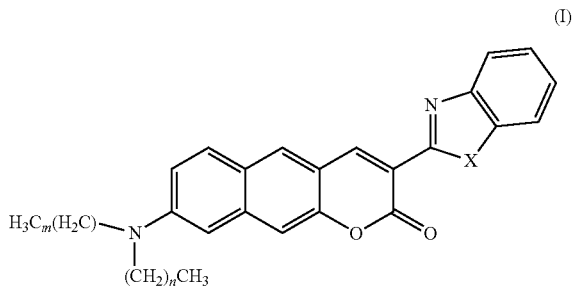

In General Formula (I), m represents an integer of 0 to 5. From the viewpoint of synthesis, m is preferably an integer of 0 to 2. From the viewpoint of solubility, n is preferably an integer of 1 to 2. m is more preferably 1.

In General Formula (I), n represents an integer of 0 to 5. From the viewpoint of synthesis, n is preferably an integer of 0 to 2. From the viewpoint of solubility, m is preferably an integer of 1 to 2. n is more preferably 1.

In General Formula (I), X is selected from the group consisting of a sulfur atom, an oxygen atom, and a group represented by NR. R is a hydrogen atom or a group represented by —$(CH_2)_y CH_3$. y represents an integer of 0 to 5. From the viewpoint of synthesis, y is preferably an integer of 0 to 2. y is more preferably 0.

Specific examples of the compound represented by General Formula (I) include the compounds listed below. However, the present invention is not limited thereto.

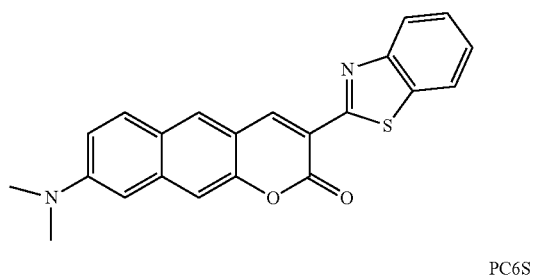

PC6S

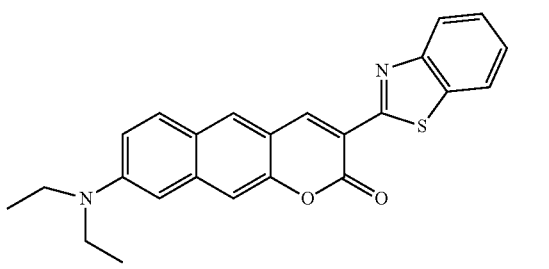

PC6O

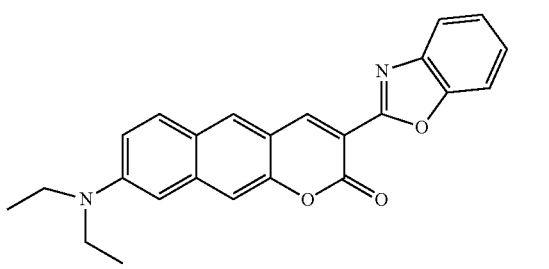

PC6NH

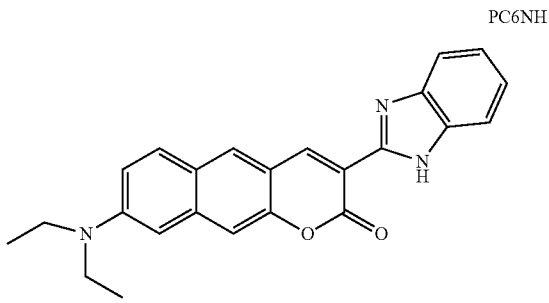

-continued

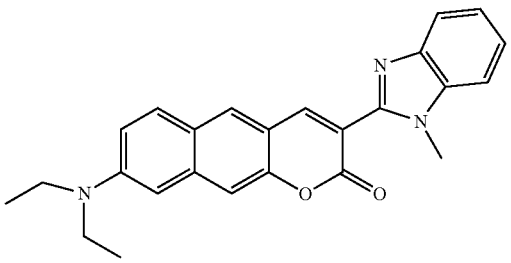

PC6NMe

Photophysical properties such as the maximum absorption/fluorescence wavelength, the fluorescence quantum yield ($\Phi_f$), and the fluorescence lifetime ($\tau_f$) of the fluorescence of the compound represented by General Formula (I) can be measured by known measurement methods. For example, the maximum absorption/fluorescence wavelength and the fluorescence yield can be measured using a luminescent quantum yield measurement apparatus or the like, for a sample in which the compound represented by General Formula (I) is dissolved in a solvent or the like. Regarding the fluorescence lifetime, the fluorescence lifetime ($\tau_f$) of the compound in each solvent can be measured using a fluorescence lifetime measurement apparatus.

The fluorescence quantum yield ($\Phi_f$) is not limited, and may be changed in accordance with the structure of the compound, the type of the solvent, and the like. It is, for example, not less than 0.5, not less than 0.7, or not less than 0.8.

The fluorescence lifetime ($\tau_f$) is not limited, and may be changed in accordance with the structure of the compound, the type of the solvent, and the like. It is, for example, not less than 2.0 ns (nanoseconds), not less than 2.5 ns, not less than 3.0 ns, or not less than 3.5 ns.

The maximum excitation wavelength of the compound represented by General Formula (I) in a solvent is not limited, and may be changed in accordance with the structure of the compound, the type of the solvent, and the like. It is, for example, 430 nm to 510 nm. The maximum fluorescence wavelength in a solvent may also be appropriately set, and may be, for example, 480 nm to 650 nm.

«Method of Producing Compound»

The compound represented by General Formula (I) may be produced based on description in the later-described Examples or a known organic synthesis method «Reagent»

The lipid droplet detection reagent of the present invention comprises a compound having the structure described above. With this structure, the reagent can have excellent photophysical properties of fluorescence (fluorescence quantum yield, fluorescence lifetime, Stokes shift, and the like). In particular, since the reagent has the excellent photophysical properties described above in various solvents, it is useful as a lipid droplet detection reagent not only for cells, but also for living individuals. Further, with the above-described structure, the reagent can have excellent lipid droplet selectivity and intracellular retention property. Thus, the reagent can be used as a highly specific lipid droplet detection reagent.

The lipid droplet detection reagent of the present invention may be composed only of the compound represented by General Formula (I), or, as long as the effect of the present invention is not inhibited, the reagent may also contain a solvent, an additive, and a compound used as a lipid droplet detection reagent other than the compound of the present invention.

<Lipid Droplet Detection Method>

One aspect of the present invention relates to a lipid droplet detection method comprising the step of administering the lipid droplet detection reagent of the present invention to a biological sample or a biological individual (other than a human) (which method may be hereinafter referred to as "lipid droplet detection method of the present invention").

Another aspect of the present invention relates to a lipid droplet detection method in which a solution containing: the lipid droplet detection reagent of the present invention; and a solubilizer; is administered to a biological sample or a biological individual (other than a human). The compound represented by General Formula (I) used as a lipid droplet detection reagent exhibits water insolubility in some cases. In such cases, the compound represented by General Formula (I) may be dissolved in an organic solvent in which the compound represented by General Formula (I) is soluble, and the resulting solution may be mixed with an aqueous solution containing a solubilizer, to prepare a solution. The prepared solution may then be administered to a biological sample or a biological individual (other than a human). The solubilizer is not limited as long as it is capable of giving water solubility to the compound represented by General Formula (I), and as long as the solubilizer has biocompatibility. Preferred examples of the solubilizer include biocompatible proteins such as albumin, gelatin, and casein. A single type of solubilizer, or a mixture of two or more types of solubilizers may be used. The solubilizer may be used at, for example, 1 to 30% by mass, preferably 5 to 20% by mass, more preferably 7.5 to 10% by mass, in an aqueous solution. Although the concentration of the compound represented by General Formula (I) may be appropriately adjusted, it may be used at, for example, 0.01 to 50 mM, preferably 0.1 to 5 mM, more preferably 0.5 to 1 mM in the solution prepared by mixing an organic solvent in which the compound represented by General Formula (I) is soluble, with an aqueous solution containing a solubilizer.

The lipid droplet detection method of the present invention may further comprise the step of detecting the lipid droplet detection reagent of the present invention. The detection of the lipid droplet detection reagent may be carried out based on a known detection method for a fluorescent reagent.

The lipid droplet detection reagent of the present invention may be used as, for example, a detection reagent for detecting lipid droplets in a biological sample. The biological sample is not limited, and may be, for example, a cell or an isolated tissue. The lipid droplet detection reagent of the present invention may also be applied to, and detected in, a living body, and may be used as a detection reagent for detecting lipid droplets in a cell, tissue, or the like in a biological individual.

The lipid droplet detection reagent of the present invention is capable of specifically detecting lipid droplets present in a cell. Thus, the reagent is useful as a detection reagent for lipid droplets in a cell.

The detection of lipid droplets present in a cell may be carried out by, for example, as follows.

The lipid droplet detection reagent of the present invention is added to a cell containing, or expected to contain, a lipid droplet.

Thereafter, a fluorescence signal of the lipid droplet detection reagent of the present invention is monitored using a fluorescence microscope or the like, to detect the lipid droplet contained in the cell.

The amount of the lipid droplet detection reagent of the present invention added to the cell may be appropriately changed in accordance with the cell used, the ratio of lipid droplets, and the like. The reagent may be added to the cell to a final concentration of, for example, 0.01 to 100 µM, preferably 0.1 to 10 µM.

In cases where the lipid droplet detection reagent of the present invention is added to the cell after dissolving the reagent in a solvent, examples of the solvent that may be used include, but are not limited to, organic solvents such as n-hexane, dibutyl ether, ethyl acetate, acetonitrile, and dimethyl sulfoxide.

The cell to which the lipid droplet detection reagent of the present invention is added is not limited as long as it is a cell containing, or expected to contain, a lipid droplet. Examples of the cell include 3T3-L1 cells and isolated adipocytes. Alternatively, a cell prepared by artificially forming lipid droplets in a cell free of lipid droplets or in a cell containing only a small amount of lipid droplets may be used. Examples of the cell free of lipid droplets or the cell containing only a small amount of lipid droplets include HeLa cells, UEET-12 cells, and NIH3T3 cells. Examples of the method of forming lipid droplets include a method in which lipid droplets are induced by a method such as addition of oleic acid to a cell.

The lipid droplet detection reagent of the present invention is also capable of specifically detecting lipid droplets in a tissue, and lipid droplets and adipose tissue in a living individual (living organism individual). Thus, the reagent is useful as a detection reagent for lipid droplets in a tissue, and lipid droplets and adipose tissue in a living body.

The detection of lipid droplets present in a tissue may be carried out by, for example, as follows.

The lipid droplet detection reagent of the present invention is added to a tissue containing, or expected to contain, a lipid droplet.

Thereafter, a fluorescence signal of the lipid droplet detection reagent of the present invention is monitored using a fluorescence microscope or the like, to detect the lipid droplet contained in the tissue.

The amount of the lipid droplet detection reagent of the present invention added to the tissue may be appropriately changed in accordance with the tissue used, the ratio of lipid droplets, and the like. The reagent may be added to the tissue to a final concentration of, for example, 0.01 to 100 µM, preferably 0.1 to 10 µM.

In cases where the lipid droplet detection reagent of the present invention is added to the tissue after dissolving the reagent in a solvent, examples of the solvent that may be used include, but are not limited to, organic solvents such as n-hexane, dibutyl ether, ethyl acetate, acetonitrile, and dimethyl sulfoxide. Further, the reagent may be administered in combination with a biocompatible liquid. Further, as described above, an organic solvent containing the lipid droplet detection reagent of the present invention may be mixed with an aqueous solution containing a solubilizer to prepare a solution, and the prepared solution may be added to the tissue.

Examples of the tissue detected with the lipid droplet detection reagent of the present invention include, but are not limited to, subcutaneous fat, visceral fat, ectopic fat (such as fat accumulated in an organ such as muscle, liver, heart, pancreas, or kidney).

The detection of lipid droplets present in a biological individual may be carried out by, for example, as follows.

The lipid droplet detection reagent of the present invention is administered to the biological individual.

Thereafter, a fluorescence signal of the lipid droplet detection reagent of the present invention is monitored using a bioimaging method using a confocal microscope or the like, to detect adipose tissue in the living body in the living state without fixation of the biological individual.

Examples of the dosage form of the lipid droplet detection reagent of the present invention include intravenous administration, subcutaneous administration, and intramuscular administration.

Although the dose of the lipid droplet detection reagent of the present invention may vary depending on the subject to which the reagent is to be administered, the dosage form, and the like, it may be administered within the range of, for example, 0.01 to 1.0 µmol/kg body weight, preferably 0.1 to 0.5 µmol/kg body weight.

In cases where the lipid droplet detection reagent of the present invention is administered to the biological individual after dissolving the reagent in a solvent, examples of the solvent that may be used include, but are not limited to, organic solvents such as n-hexane, dibutyl ether, ethyl acetate, acetonitrile, and dimethyl sulfoxide. Further, the reagent may be administered in combination with a biocompatible liquid. Further, as described above, an organic solvent containing the lipid droplet detection reagent of the present invention may be mixed with an aqueous solution containing a solubilizer to prepare a solution, and the prepared solution may be added to the biological individual.

Examples of the organism individual to which the reagent is to be administered include, but are not limited to, vertebrates including mammals (such as mice, pigs, dogs, rabbits, and humans), and invertebrates.

<Compound of Present Invention>

The compound represented by the following General Formula (I)' is a novel compound synthesized by the present invention. Thus, one aspect of the present invention relates to a compound presented by the following General Formula (I)' (which may be hereinafter referred to as "compound of the present invention").

The compound represented by General Formula (I)' is a compound having the following structure.

In General Formula (I)', m represents an integer of 0 to 5. From the viewpoint of synthesis, m is preferably an integer of 0 to 2. From the viewpoint of solubility, m is preferably an integer of 1 to 2. m is more preferably 1.

In General Formula (I)', n represents an integer of 0 to 5. From the viewpoint of synthesis, n is preferably an integer of 0 to 2. From the viewpoint of solubility, m is preferably an integer of 1 to 2. n is more preferably 1.

In General Formula (I)', X is selected from the group consisting of an oxygen atom, and a group represented by NR'. R' is a group represented by —$(CH_2)_y CH_3$, and y represents an integer of 0 to 5. From the viewpoint of synthesis, y is preferably an integer of 0 to 2. y is more preferably 0.

EXAMPLES

The present invention is described below concretely by way of Examples. However, these are exemplification of the present invention, and the scope of the present invention is not limited to these.

Synthesis Examples

The compounds PC6S, PC6O, PC6NH, and PC6NMe were synthesized as follows.

Scheme 1 illustrates the synthetic pathway of PC6S, PC6O, PC6NH, and PC6NMe.

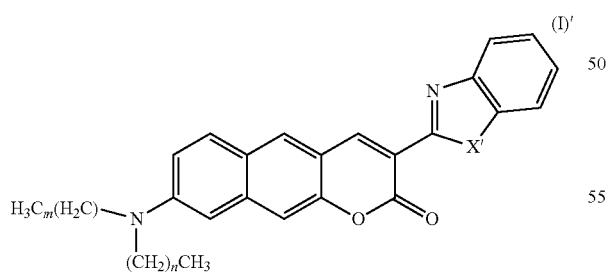

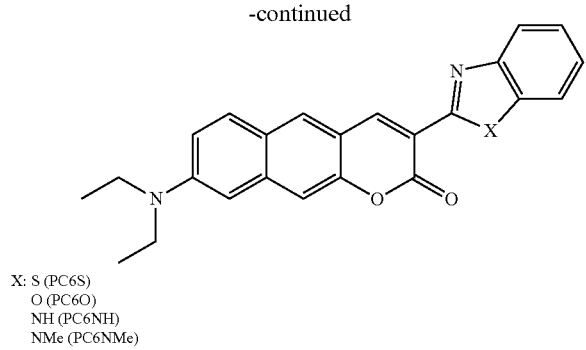

X: S (PC6S)
O (PC6O)
NH (PC6NH)
NMe (PC6NMe)

7-(Diethylamino)naphthalen-2-ol (1)

A mixture of 2,7-dihydroxynaphthalene (3.0 g, 18.7 mmol), sodium disulfite (7.11 g, 37.4 mmol), diethylamine (9.7 mL, 93.5 mmol), and water (7 mL) was stirred at 140° C. for 6 hours using a seal tube. After cooling in air, dichloromethane was added to the reaction solution, and washing with water was carried out several times. The organic layer was concentrated by drying over anhydrous sodium sulfate. The resulting crude product was purified (silica gel column; developing solvent, n-hexane:ethyl acetate (4:1, v/v)) using a flash automatic purification apparatus (Isolera Spektra, Biotage), to obtain Compound 1 (yield: 1.26 g, 31%).

$^1$H NMR (400 MHz, CDCl$_3$, TMS): δ 7.59-7.53 (2H, q), 6.94-6.90 (2H, m), 6.76-6.73 (1H, d) 6.69 (1H, s), 4.78 (1H, br), 3.46-3.41 (4H, q), 1.22-1.18 (6H, t)

[7-(Methoxymethoxylamino)naphthalen-2-yl]diethylamine (2)

Compound 1 (0.86 g, 4 mmol) was dissolved in anhydrous DMF, and cooled to −15° C. in an ice bath. After addition of sodium hydride (250 mg, 10.4 mmol), the resulting mixture was stirred until the generation of hydrogen ended. To this solution, chloromethyl methyl ether (0.38 mL, 5.0 mmol) was added, and the resulting mixture was stirred at room temperature for 6 hours. The reaction solution was poured onto water, and extracted with ethyl acetate. The organic layer was concentrated by drying over anhydrous sodium sulfate. The resulting crude product was purified (silica gel column; developing solvent, n-hexane:ethyl acetate (9:1, v/v)) using a flash automatic purification apparatus (Isolera Spektra, Biotage), to obtain Compound 2 (yield: 0.91 g, 88%).

$^1$H NMR (400 MHz, CDCl$_3$, TMS): δ 7.60-7.55 (2H, q), 7.17 (1H, s), 6.96-6.93 (1H, d), 6.89-6.86 (1H, d), 6.78 (1H, s), 5.27 (2H, s), 3.46-3.41 (4H, q), 1.22-1.18 (6H, t)

6-Diethylamino-3-(methoxymethoxyl)naphthalene-2-carbaldehyde (3)

Compound 2 (2.80 g, 10.8 mmol) was dissolved in anhydrous diethyl ether, and t-butyllithium (1.9 mol/L solution in pentane; 8.5 mL, 16.2 mmol) was added to the resulting mixture at −20° C. for 30 minutes, followed by stirring the mixture for 2 hours. To this solution, anhydrous DMF (25 mL, 320 mmol) was added, and the resulting mixture was stirred at −20° C. for 1 hour. After adding 4 N HCl (10 mL) thereto, the mixture was stirred at −20° C. for 30 minutes. Ethyl acetate was added to the reaction solution, and the organic layer was washed several times with 0.5 N HCl, saturated aqueous sodium hydrogen carbonate solution, and brine. The organic layer was concentrated by drying over anhydrous sodium sulfate. The resulting crude product was purified (silica gel column; developing solvent, n-hexane:ethyl acetate (9:1, v/v)) using a flash automatic purification apparatus (Isolera Spektra, Biotage), to obtain Compound 3 (yield: 2.45 g, 79%).

$^1$H NMR (400 MHz, CDCl$_3$, TMS): δ 10.43 (1H, s), 8.19 (1H, s), 7.69-7.66 (1H, d), 7.15 (1H, s), 6.95-6.93 (1H, d), 6.69 (1H, s), 5.36 (2H, s), 3.55 (3H, s), 3.49-3.44 (4H, q), 1.24-1.21 (6H, t)

6-Diethylamino-3-(hydroxy)naphthalene-2-carbaldehyde (4)

Compound 3 (1.59 g, 5.5 mmol) was dissolved in 2-propanol:5 N HCl (70 mL:35 mL), and the resulting solution was stirred at 60° C. for 4 hours. From the reaction solution, 2-propanol was evaporated under reduced pressure. After adding ethyl acetate thereto, the organic layer was washed with water several times. The organic layer was concentrated by drying over anhydrous sodium sulfate. The resulting crude product was purified (silica gel column; developing solvent, n-hexane:ethyl acetate (4:1, v/v)) using a flash automatic purification apparatus (Isolera Spektra, Biotage), to obtain Compound 4 (yield: 1.31 g, 98%).

$^1$H NMR (400 MHz, CDCl$_3$, TMS): δ 10.53 (1H, s), 9.85 (1H, s), 7.85 (1H, s), 7.66-7.63 (1H, d), 6.93-6.90 (1H, d), 6.90 (1H, s), 6.60 (1H, s), 3.51-3.45 (4H, q), 1.28-1.22 (6H, t)

3-(Benzo[d]thiazol-2-yl)-8-(diethylamino)-2H-benzo[g]chromen-2-one (PC6S)

Compound 4 (120 mg, 0.49 mmol) and 2-(2-benzothiazolyl)ethyl acetate (122 mg, 0.55 mmol) were dissolved in anhydrous ethanol, and about five drops of piperidine was added to the resulting solution, followed by stirring the solution at 60° C. for 4 hours. After removing the precipitated solids by filtration, the filtrate was purified (silica gel column; developing solvent, n-hexane:ethyl acetate (1:1, v/v)) using a flash automatic purification apparatus (Isolera Spektra. Biotage), to obtain Compound PC6S (yield: 157 mg, 80%).

$^1$H NMR (400 MHz, CDCl$_3$, TMS): δ 9.08 (1H, s), 8.08-8.06 (1H, d), 7.99 (1H, s), 7.97-7.95 (1H, d), 7.79-7.77 (1H, d), 7.53-7.49 (1H, t), 7.44 (1H, s), 7.41-7.38 (1H, t), 7.11-7.08 (1H, d), 6.79 (1H, s), 3.55-3.49 (4H, q), 1.29-1.25 (6H, t).

ESI-MS (m/z) of PC6S: calcd for $C_{24}H_{21}N_2O_2S$ [M+H]$^+$: 401.12, found: 401.2

3-(Benzo[d]oxazol-2-yl)-8-(diethylamino)-2H-benzo[g]chromen-2-one (PC6O)

Compound 4 (122 mg, 0.50 mmol) and 2-(2-benzoxazolyl)ethyl acetate (120 mg, 0.59 mmol) were dissolved in anhydrous ethanol, and about five drops of piperidine was added to the resulting solution, followed by stirring the solution at 60° C. for 4 hours. After removing the precipitated solids by filtration, the filtrate was purified (silica gel column; developing solvent, n-hexane:ethyl acetate (1:1, v/v)) using a flash automatic purification apparatus (Isolera Spektra. Biotage), to obtain Compound PC6O (yield: 138 mg, 72%).

¹H NMR (400 MHz, CDCl₃, TMS): δ 8.79 (1H, s), 7.93 (1H, s), 7.86-7.84 (1H, t), 7.77-7.75 (1H, d), 7.63-7.61 (1H, t), 7.40 (1H, s), 7.38-7.36 (1H, t), 7.11-7.08 (1H, d), 6.78 (1H, s), 3.55-3.50 (4H, q), 1.29-1.25 (6H, t).

ESI-MS (m/z) of PC6O calcd for $C_{24}H_{21}N_2O_3$ [M+H]⁺: 385.15, found: 385.2

3-(1H-Benzo[d]imidazol-2-yl)-8-(diethylamino)-2H-benzo[g]chromen-2-one (PC6NH)

Compound 4 (80 mg, 0.36 mmol) and 2-(2-benzimidazolyl)ethyl acetate (100 mg, 0.49 mmol) were dissolved in anhydrous ethanol, and about five drops of piperidine was added to the resulting solution, followed by stirring the solution at 60° C. for 4 hours. After removing the precipitated solids by filtration, the filtrate was purified (silica gel column, developing solvent, chloroform:methanol (97:3, v/v)) using a flash automatic purification apparatus (Isolera Spektra, Biotage), to obtain Compound PC6NH (yield: 64 mg, 46%).

¹H NMR (400 MHz, CDCl₃, TMS): δ 11.31 (1H, s), 9.11 (1H, s), 7.95 (1H, s), 7.80-7.77 (1H, t), 7.55-7.51 (1H, m), 7.44 (1H, s), 7.30-7.29 (1H, t), 7.12-7.09 (1H, d), 6.79 (1H, s), 3.55-3.49 (4H, q), 1.29-1.25 (6H, t).

ESI-MS (m/z) of PC6NH calcd for $C_{24}H_{22}N_3O_2$ [M+H]⁺: 384.16, found: 384.1

8-(Diethylamino)-3-(1-methyl-1H-benzo[d]imidazol-2-yl)-2H-benzo[g]chromen-2-one (PC6NMe)

Compound 4 (80 mg, 0.36 mmol) and 2-(1-methyl-2-benzimidazolyl)ethyl acetate (100 mg, 0.46 mmol) were dissolved in anhydrous ethanol, and about five drops of piperidine was added to the resulting solution, followed by stirring the solution at 60° C. for 4 hours. After removing the precipitated solids by filtration, the filtrate was purified (silica gel column; developing solvent, chloroform:methanol (97:3, v/v)) using a flash automatic purification apparatus (Isolera Spektra, Biotage), to obtain Compound PC6NMe (yield: 40 mg, 28%).

¹H NMR (400 MHz, CDCl₃, TMS): δ 8.37 (1H, s), 7.88 (1H, s), 7.81-7.80 (1H, d), 7.77-7.72 (1H, m), 7.44 (1H, s), 7.43-7.41 (1H, d), 7.34-7.29 (2H, m), 7.11-7.08 (1H, d), 6.80 (1H, s), 3.85 (3H, s), 3.54-3.49 (4H, q), 1.29-1.25 (6H, t).

ESI-MS (m/z) of PC6NMe calcd for $C_{25}H_{24}N_3O_2$ [M+H]⁺: 398.18, found: 398.1

3-(Benzo[d]thiazol-2-yl)-8-(dimethylamino)-2H-benzo[g]chromen-2-one

Based on the Scheme 1 described above, the captioned compound was synthesized.

¹H NMR (400 MHz, CDCl₃, TMS): δ 9.08 (1H, s), 8.08-8.06 (1H, d), 7.99 (1H, s), 7.97-7.95 (1H, d), 7.79-7.77 (1H, d), 7.53-7.49 (1H, t), 7.44 (1H, s), 7.41-7.38 (1H, t), 7.11-7.08 (1H, d), 6.79 (1H, s), 3.55-3.49 (6H, t).

<Measurement Method>
(Measurement of Maximum Absorption Wavelength, Maximum Fluorescence Wavelength, and Fluorescence Quantum Yield)

Using a luminescent quantum yield measurement apparatus (C9920-01, manufactured by Hamamatsu Photonics K.K.), the maximum absorption wavelength (λabs/nm), the maximum fluorescence wavelength (λflu/nm), and the fluorescence quantum yield ($\Phi_f$) of the compound in each solvent were measured.

The absorption spectrum was measured using an ultraviolet and visible spectrophotometer (Ubest-550, manufactured by JASCO Corporation), and the fluorescence emission spectrum was measured using a fluorescence spectrophotometer (F-7000, manufactured by Hitachi, Ltd.)

(Measurement of Fluorescence Lifetime)

The fluorescence lifetime ($\tau_f$) of each compound in each solvent was measured using a compact fluorescence lifetime measurement apparatus (Quntaurus-Tau, manufactured by Hamamatsu Photonics K.K.).

The fluorescence yield, that is, the fluorescence quantum yield ($\Phi_f$), represents the ratio of photons emitted as fluorescence out of the photons absorbed in a substance. Thus, the higher the fluorescence yield, the higher the luminescence efficiency and the higher the luminescence intensity. The value of the fluorescence lifetime ($\tau_f$) is unique to the molecule.

(Measurement of Photostability and Retention Property)

Using a fluorescence microscope (IX71, manufactured by Olympus Corporation), fluorescence imaging images of cells were acquired over time, and the photostability ($I_t/I_0$) and the retention property were measured.

Example 1

Figure 3:
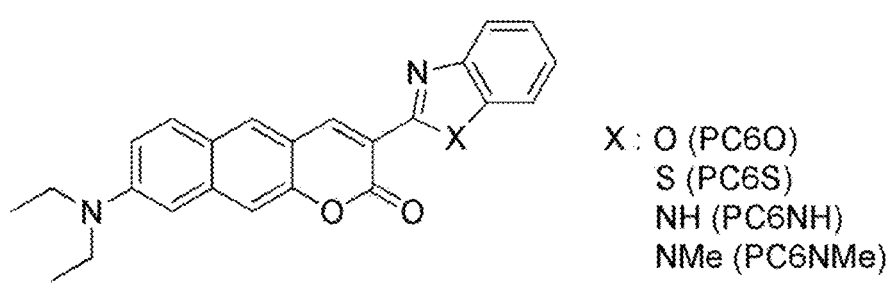
FIG. 3 shows the structural formula of a compound according to one aspect of the present invention, synthesized in Examples.

The compounds of the present invention synthesized in the above production examples (FIG. 3; PC6S, PC6O, PC6NH, and PC6NMe) contain an 8-diethylaminobenzocoumarine skeleton. These compounds were subjected to measurement of photophysical properties.

Figure 4:
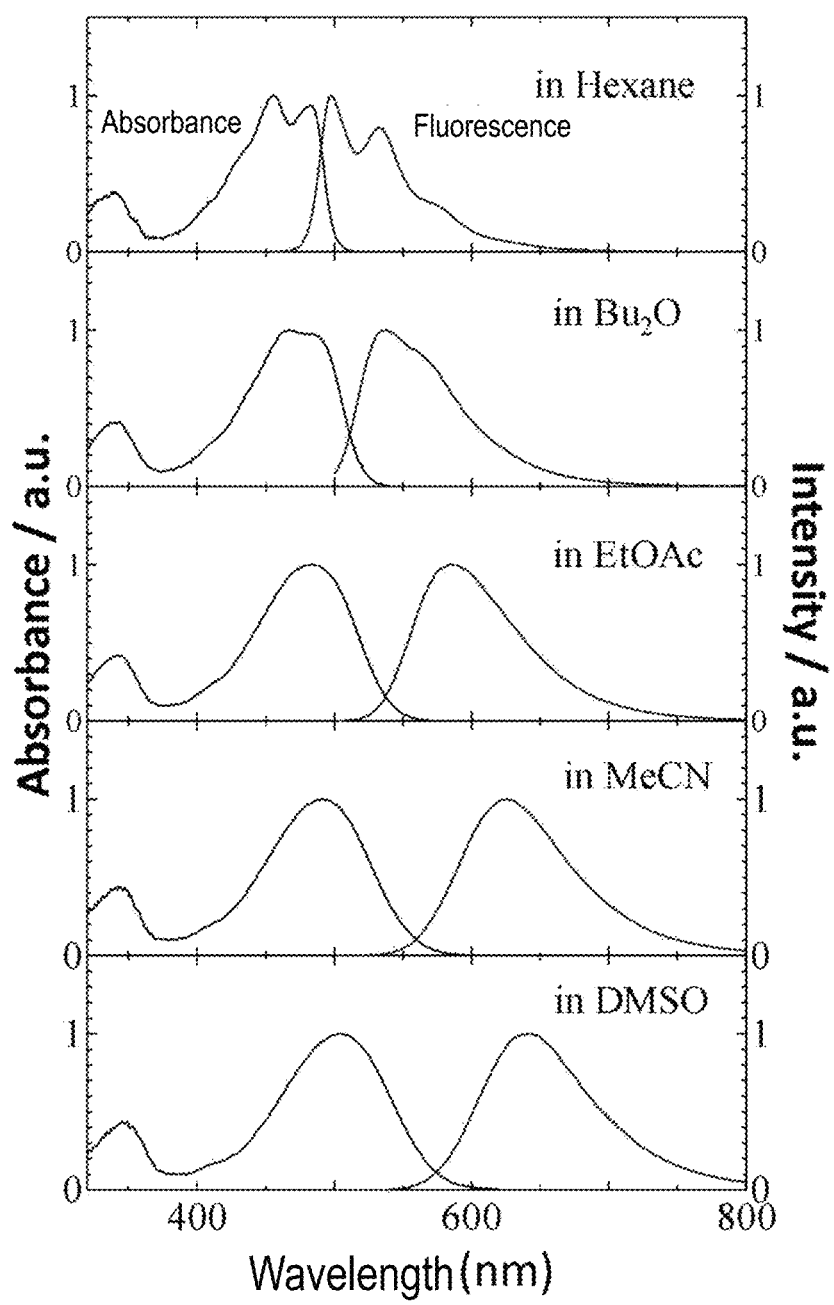
FIG. 4 shows the absorption and fluorescence spectra of a compound of the present invention (PC6S).

FIG. 4 shows the absorption and fluorescence spectra of PC6S in each solvent. Table 1 shows photophysical parameters. The maximum absorption wavelength was found at 455 to 504 nm, and the maximum fluorescence wavelength was found at 498 to 642 nm. Each maximum wavelength exhibited a shift toward longer wavelength as the polarity of the solvent increased. The fluorescence quantum yield was not less than 0.8 in any of the solvents.

TABLE 1

Figure 5:
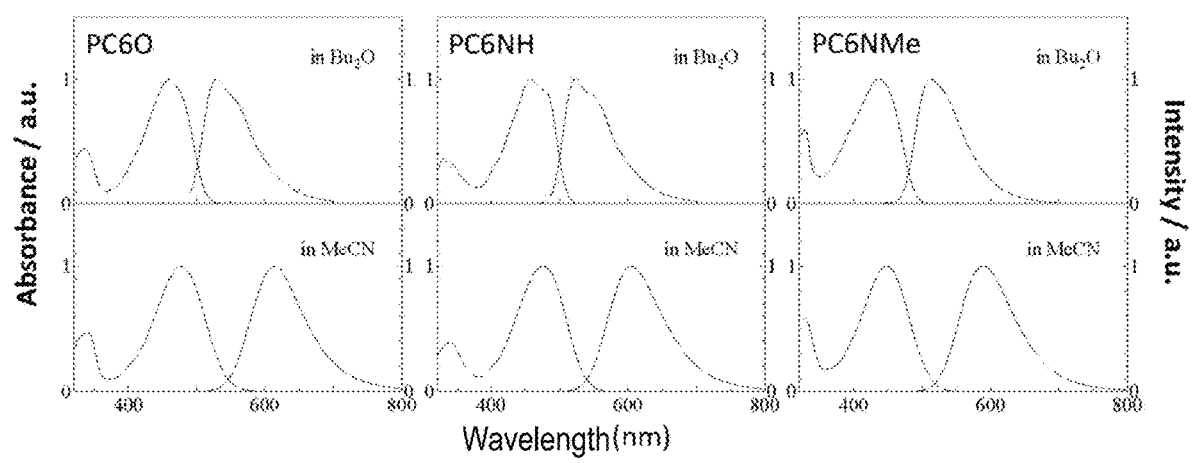
FIG. 5 shows the absorption and fluorescence spectra of compounds according to one aspect of the present invention (PC6O, PC6NH, PC6NMe).

| solvents | ε | $\lambda_{max}^{abs}$/nm | $\lambda_{max}^{flu}$/nm | $\Phi_f$ | $\tau_f$/ns |
|---|---|---|---|---|---|
| n-Hexane | 1.89 | 455 | 498 | 0.89 | 2.55 |
| Bu₂O | 3.08 | 468 | 538 | 0.88 | 2.91 |
| EtOAc | 6.08 | 483 | 585 | 0.84 | 3.41 |
| MeCN | 36.6 | 492 | 625 | 0.80 | 3.72 |
| DMSO | 49.5 | 504 | 642 | 0.83 | 3.46 | n-Hexane: n-Hexane
Bu₂O: Dibutyl ether
EtOAc: Ethyl acetate
MeCN: Acetonitrile
DMSO: Ditnethyl sulfoxide
ε: Dielectric constant
$\lambda_{max}^{abs}$: Maximum absorption wavelength
$\lambda_{max}^{flu}$: Maximum flourescence wavelength
$\Phi_f$: Flourescence quantum yield
$\tau_f$: Flourescence lifetime FIG. 5 shows the absorption and fluorescence spectra of PC6O, PC6NH, and PC6NMe in dibutyl ether or acetonitrile, and Table 2 shows photophysical parameters.

TABLE 2

| probe | Solvents | $\lambda_{max}^{abs}$/nm | $\lambda_{max}^{flu}$/nm | $\Phi_f$ | $\tau_f$/ns |
|---|---|---|---|---|---|
| PC6S | Bu₂O | 468 | 538 | 0.88 | 2.91 |
| | MeCN | 493 | 625 | 0.80 | 3.72 |

TABLE 2-continued

| probe | Solvents | $\lambda_{max}^{abs}$/nm | $\lambda_{max}^{flu}$/nm | $\Phi_f$ | $\tau_f$/ns |
|---|---|---|---|---|---|
| PC6O | Bu$_2$O | 460 | 530 | 0.86 | 2.83 |
|  | MeCN | 478 | 613 | 0.80 | 3.70 |
| PC6NH | Bu$_2$O | 458 | 523 | 0.89 | 2.79 |
|  | MeCN | 477 | 604 | 0.82 | 3.78 |
| PC6NMe | Bu$_2$O | 438 | 512 | 0.67 | 3.53 |
|  | MeCN | 449 | 590 | 0.77 | 4.08 |

$\lambda_{max}^{abs}$: Maximum absorption wavelength
$\lambda_{max}^{flu}$: Maximum flourescence wavelength
$\Phi_f$: Flourescence quantum yield
$\tau_f$: Flourescence lifetime

Example 2

Concerning imaging of lipid droplets in cultured cells, an experiment was carried out for comparison of the performance between PC6S and commercially available lipid droplet fluorescence imaging reagents (LipiDye, Nile Red, BODIPY493/503, and Lipi Green). The following items were investigated, the luminescence intensity, the lipid droplet selectivity, the photostability, and the retention property.

Figure 6:
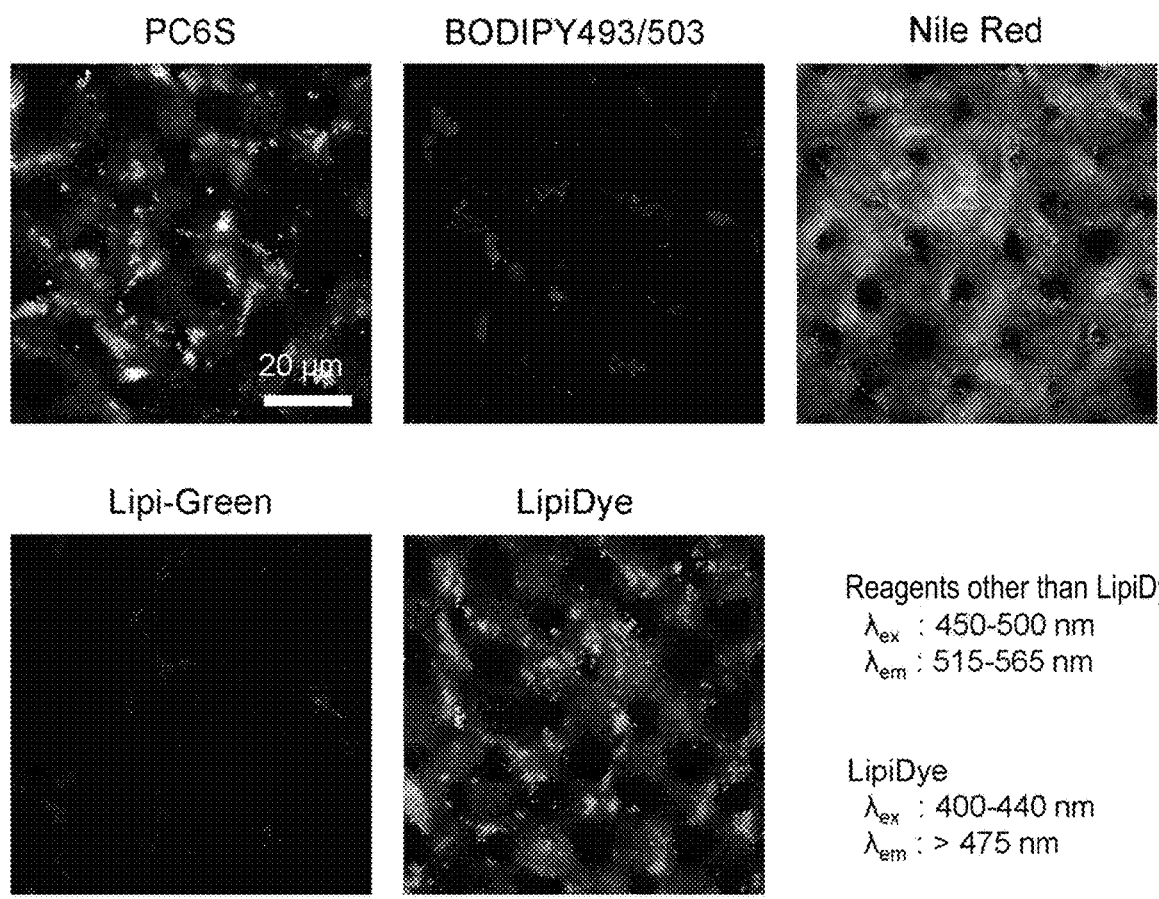
FIG. 6 shows fluorescence imaging images obtained by adding PC6S or a commercially available lipid droplet imaging reagent to HeLa cells (drawing-substituting photographs).

FIG. 6 shows fluorescence imaging images obtained by culturing HeLa cells for 48 hours in the presence of 400 μM oleic acid, adding each fluorescent reagent to a final concentration of 100 nM, performing culture for 30 minutes, washing the cultured cells, and then carrying out observation using an inverted fluorescence microscope (IX71, manufactured by Olympus Corporation) (objective lens, ×100 oil immersion; excitation wavelength, 450 to 500 nm; monitoring wavelength, 515 to 565 nm; LipiDye: excitation wavelength, 400 to 440 nm; monitoring wavelength, >475 nm). It can be seen that the HeLa cells to which PC6S, LipiDye, or Nile Red was added exhibited higher fluorescence intensities than the HeLa cells to which BODIPY493/503 or Lipi Green was added. Furthermore, although PC6S and LipiDye were capable of clear imaging of lipid droplets in the HeLa cells, Nile Red produced fluorescence signals also from organelles other than lipid droplets. This indicates low lipid droplet selectivity of Nile Red, which is consistent with a past report. Although LipiDye is a reagent that exhibits a green fluorescence, general-purpose filters for green fluorescent reagents cannot be used therefor (according to a note described in the reagent HP). Since LipiDye requires use of an excitation wavelength of about 405 nm, there is a concern about phototoxicity to cells in cases of long observation.

Figure 7:
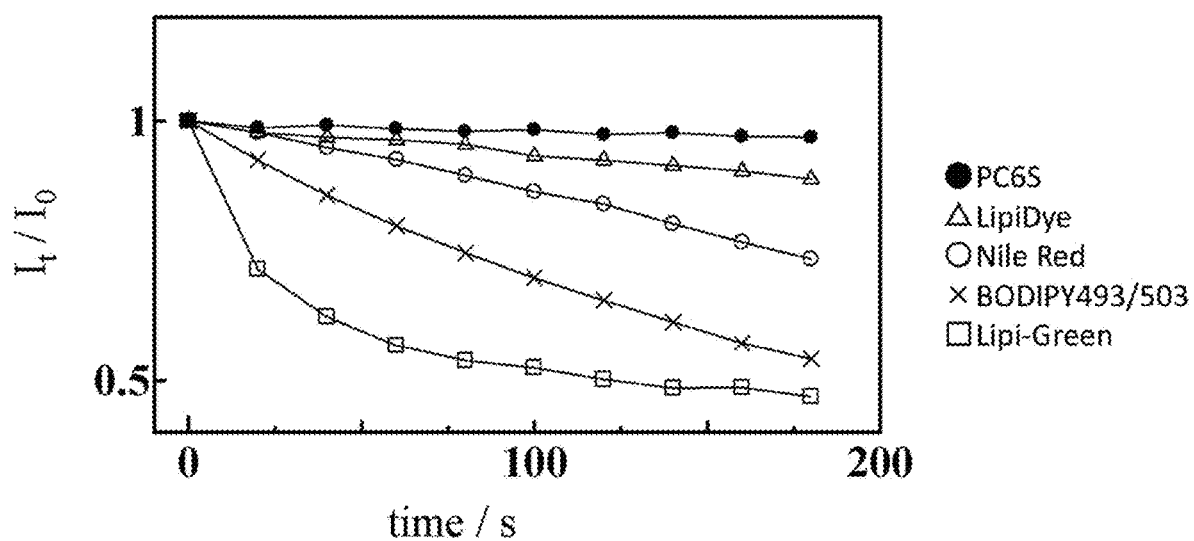
FIG. 7 shows evaluation results on the intracellular photostabilities of PC6S and commercially available lipid droplet imaging reagents.

The photostability and the retention property are important factors in long-term measurement for, for example, tracing the processes of formation, fusion, and degradation of lipid droplets. Each fluorescent reagent was added to 3T3-L1 cells (adipocytes) to a final concentration of 100 nM, and the cells were cultured for 30 minutes. After washing the cells, the cells were irradiated with an excitation light required for imaging (450 to 500 nm; for LipiDye, an excitation wavelength of 400 to 440 nm), to evaluate the photostability. By regarding the time immediately after the irradiation as Second 0, imaging images were acquired at 20-second intervals for analysis of the image intensity. FIG. 7 shows plots of the fluorescence intensity ratio ($I_t/I_0$) against the irradiation time. PC6S was found to have the highest photostability relative to the commercially available reagents.

Figure 8:
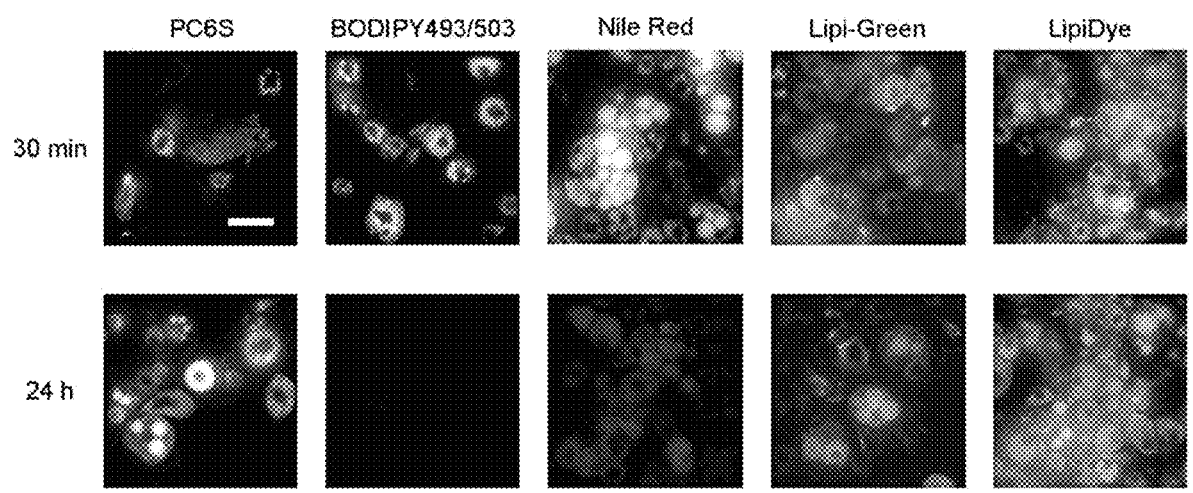
FIG. 8 shows evaluation results on the intracellular retention properties of PC6S and commercially available lipid droplet imaging reagents (drawing-substituting photographs).

For evaluation of the intracellular retention property of each reagent, each fluorescent reagent was added to 3T3-L1 cells (adipocytes) to a final concentration of 100 nM (for Lipi-Green, 500 nM), and imaging images were acquired after 30 minutes of culture and 24 hours after washing away of the reagent. FIG. 8 shows the fluorescence imaging images. While PC6S, Lipi-Green, and LipiDye were capable of imaging of lipid droplets even 24 hours later, BODIPY493/503 and Nile Red exhibited remarkable decreases in the fluorescence intensity. It was thus shown that PC6S, Lipi-Green, and LipiDye have high intracellular retention properties.

The above results are summarized in Table 3. According to Table 3, it was revealed that PC6S has better properties compared to those of the commercially available lipid droplet fluorescence imaging reagents.

TABLE 3

|  | Reagent of the invention PC6S | Commercially available reagent ||||
|---|---|---|---|---|---|
|  |  | BODIPY 493/503 | Nile Red | Lipi-Green | LipiDye |
| Brightness in cells | ◎ | Δ | ○ | Δ | ○ |
| Selectivity for lipid droplets | ○ | ○ | X | ○ | ○ |
| Application of general-purpose filters | ◎ | ○ | X | ◎ | X |
| Photostability | ◎ | X | Δ | X | ○ |
| Intracellular retention property | ◎ | X | Δ | ◎ | ◎ |
| Imaging of lipid dropletts in a tissue | ◎ | — | — | — | — |

Example 3

Fluorescence imaging of lipid droplets in a body tissue, and of an adipose tissue, using PC6S is described below. Since PC6S has remarkably low solubility in water (physiological saline), it is difficult to directly allow its dissolution. Further, in cases where 5 mM stock solution in dimethyl sulfoxide (DMSO) is added (at 10% in terms of the volume ratio) to physiological saline, precipitation of PC6S occurs. Therefore, PC6S cannot be administered to mice. In view of this, 5 mM stock solution was added (at 10% in terms of the volume ratio) to physiological saline supplemented with 10% bovine serum albumin. As a result, precipitation of PC6S could be suppressed. Regarding administration of MNs-NB, a stock solution in DMSO is directly administered to mice. Since administration of DMSO may cause death of mice from shock, the administration method in the present invention is thought to be a safer method. Here, 100 to 200 μL of 500 μM solution (50 to 100 nmol) was administered to the tail vein of a mouse under anesthesia, and a fluorescence imaging experiment was carried out using a confocal laser microscope (excitation wavelength, 488 nm; monitoring wavelength, 510 to 560 nm). In the present experiment, a microscope capable of acquiring fluorescence lifetime images as well as fluorescence intensity images (FLIM: fluorescence lifetime imaging microscope) (Simple-Tau-150-DX; Becker & Hickl) was used. The animal experiment was carried out in accordance with the animal experiment safety regulations in Gunma University.

Figure 9:
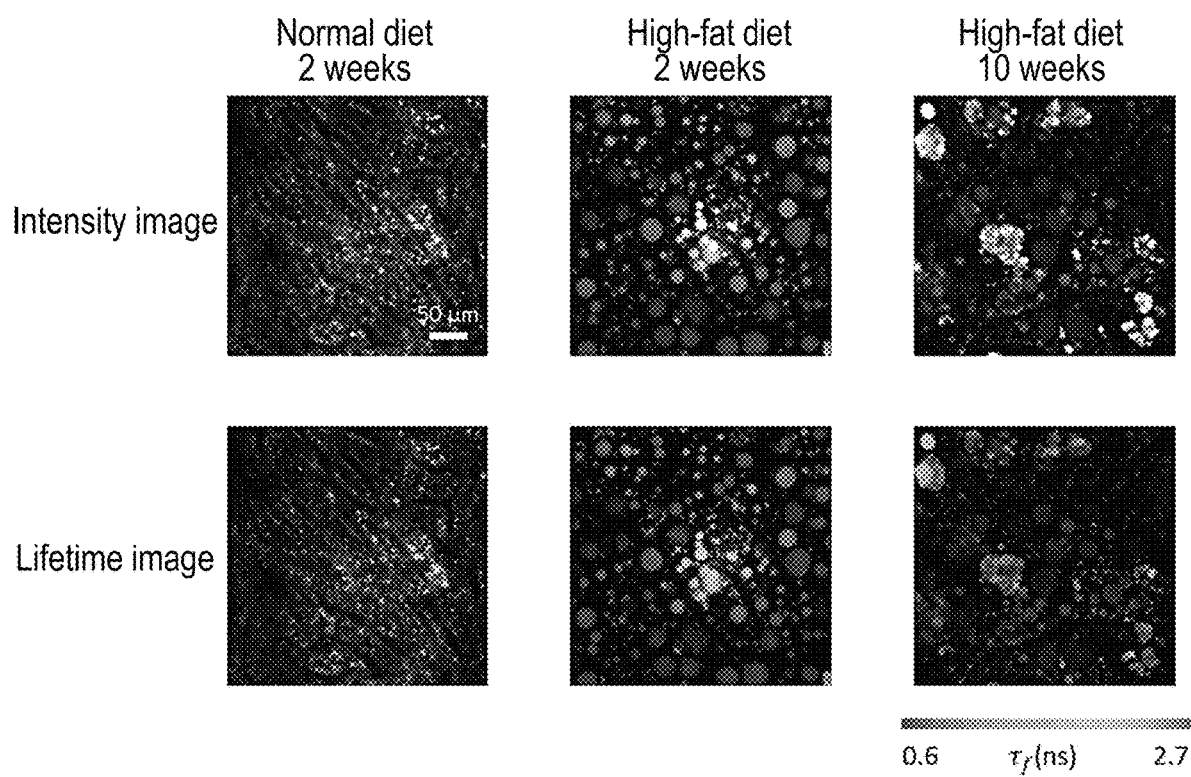
FIG. 9 shows intensity images and lifetime images of the liver surface of mice to which PC6S was administered (drawing-substituting photographs).

Fatty-liver model mice are known to have a liver containing a larger amount of lipid droplets accumulated therein compared to normal mice. Here, fatty-liver model mice were prepared by feeding mice (C57BL/6J) with an ultra-high-fat, choline-deficient, methionine-reduced diet for 2 weeks or 10 weeks. FIG. 9 shows fluorescence intensity imaging images and fluorescence lifetime imaging images obtained by administration of 100 nmol of PC6S to a normal mouse and fatty-liver model mice. In the mouse fed with a normal diet, small lipid droplets could be found in hepatocytes. On the other hand, in a fatty-liver model mouse (Week 2), large lipid droplets were imaged over the entire liver surface, thus indicating accumulation of lipid in the liver. Furthermore, in the mouse fed with the fatty diet for 10 weeks, intense fluorescence was found from structures having shapes different from those of lipid droplets, in addition to the fluorescence from lipid droplets. This is thought to be autofluorescence due to infiltration of macrophage-derived cells caused by liver fibrosis. Unlike intensity imaging, which is not capable of clear imaging of lipid droplets, lifetime imaging allows imaging capable of distinguishing between the autofluorescence (blue) and the PC6S fluorescence (orange).

Figure 10:
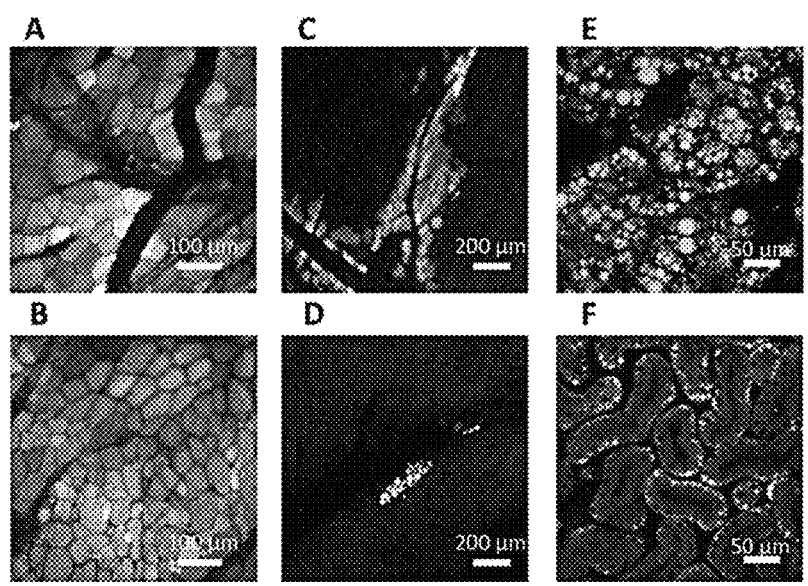
FIG. 10 shows fluorescence intensity imaging images of adipose tissue and lipid droplets in a mouse to which PC6S was administered (drawing-substituting photographs). Fluorescence imaging images of subcutaneous adipose tissue (Panel A), abdominal adipose tissue (Panel B), skeletal muscle (Panel C), cardiac muscle (Panel D), pericardial adipose tissue (Panel E), and kidney (Panel F) are shown.

In an individual, various adipose tissues and lipid droplets are present. Their imaging was carried out using PC6S. FIG. 10 shows fluorescence imaging images of subcutaneous adipose tissue, abdominal adipose tissue, skeletal muscle, cardiac muscle, pericardial adipose tissue, and kidney, obtained by administration of 50 nmol of PC6S to a mouse (BALB/cAJcl). The imaging images of the cardiac muscle and the pericardial adipose tissue were taken after euthanization of the mouse and removal of those tissues. Fluorescence derived from PC6S was found from sites containing lipid accumulated therein. In particular, for the kidney, small lipid droplets distributed in tubular cells could be imaged. It is therefore expected that PC6S may be useful as a tool for studying the association of lipid with lifestyle-related diseases such as diabetes, and with renal disfunction.

Example 4

Figure 11:
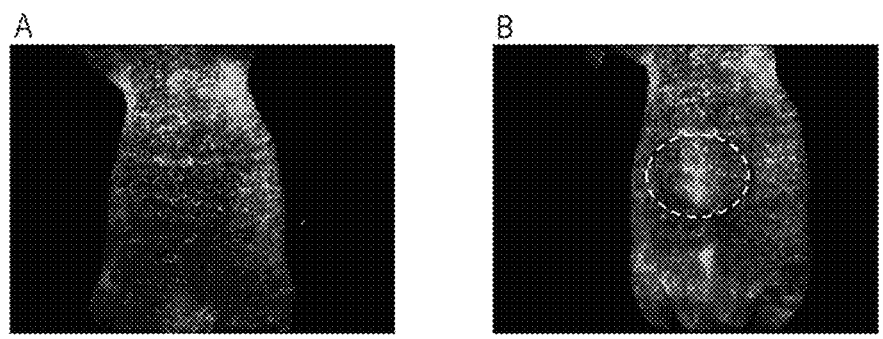
FIG. 11 shows non-laparotomic imaging images of adipose tissue and lipid droplets in a mouse subjected to PC6S administration (drawing-substituting photographs). Panel A shows an image before the PC6S administration (mouse autofluorescence), and Panel B shows an image after the PC6S administration.

Non-laparotomic imaging of lipid droplets in a body tissue, and of an adipose tissue, using PC6S is described below. A nude mouse was fed with a high-fat diet for 2 weeks to prepare a fatty-liver model mouse. PC6S (50 nmol) was administered from the tail vein of the nude mouse under anesthesia. Images were taken using a simple in vivo imaging device (Discovery (registered trademark); INDEC BioSystem) (for the nude mice lying on its back). An excitation wavelength of 450 to 490 nm and a monitoring wavelength of 520 nm or higher were employed. FIG. 11 shows non-laparotomic imaging images of the nude mouse. Fluorescence derived from PC6S was found around the liver (the portion surrounded by a dotted line).

Figure 12:
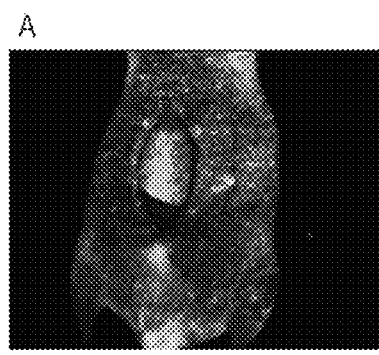
FIG. 12 shows non-laparotomic imaging images of adipose tissue and lipid droplets in a mouse subjected to PC6S administration (drawing-substituting photographs). Panel A shows an image taken after peeling off the skin, and Panel B shows an image taken after peeling off the skin and the membrane covering the organs.
Figure 12:
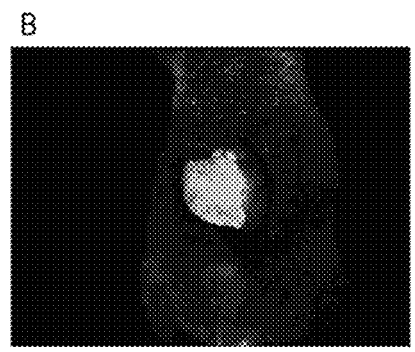

In order to confirm that the fluorescence was found from the liver, an image was taken after laparotomy. FIG. 12 shows laparotomic imaging images of the nude mouse. Fluorescence derived from PC6S was found in the liver. It was thus shown that the fluorescence imaging reagent of the present invention is useful even without laparotomy.

The fluorescence imaging reagent of the present invention is applicable to, and allows the detection in, unfixed biological samples and living bodies. The reagent is, however, also useful for fixed samples. HeLa cells cultured in the presence of 400 μM oleic acid for 48 hours were fixed in 4% paraformaldehyde-phosphate buffer for 20 minutes, and PC6S was added thereto to a final concentration of 100 nM, followed by performing culture for 30 minutes, washing the cultured cells, and then acquiring a fluorescence imaging image using an inverted fluorescence microscope in the same manner as in Example 2. As a result, fluorescence of PC6S could be detected also in the fixed HeLa cells.

Further, by combined use of PC6S with Hoechst 33342 and Mito tracker red, multicolor imaging was possible.

Further, HeLa cells were cultured for 30 minutes in a medium to which PC6S was added to a final concentration of 100 nM, and PC6S unincorporated in the cells was removed, followed by acquiring a fluorescence imaging image (Hour 0) using an inverted fluorescence microscope in the same manner as in Example 2. The cells were cultured in the presence of 400 μM oleic acid for 24 hours, and their fluorescence imaging images were acquired 4, 8, 12, and 24 hours later. As a result, the process of gradual formation of lipid droplets could be imaged over time.

Further, HeLa cells were plated on a 96-well plate, and allowed to adhere to a glass surface. Thereafter, PC6S was added to the medium (to a final concentration of 0.1, 0.5, 1, 10, 20, 40, or 50 μM), and culture was performed for 24 hours. After washing, cytotoxicity was evaluated using a cell growth-cytotoxicity measurement kit CCK-8. Two hours after the addition of the reagent, the absorbance was measured. As a result, no remarkable cytotoxicity was found at any concentration.

According to the above results, the fluorescence imaging reagent developed by the present invention was found to be a novel reagent capable of imaging of intracellular lipid droplets, and adipose tissues and lipid droplets in living individuals.

INDUSTRIAL APPLICABILITY

The present invention can be used for fluorescence imaging of lipid droplets in biological samples and biological individuals.

The invention claimed is:

1. A lipid droplet detection method comprising the step of: administering to a biological sample or a biological individual, a compound of Formula (I):

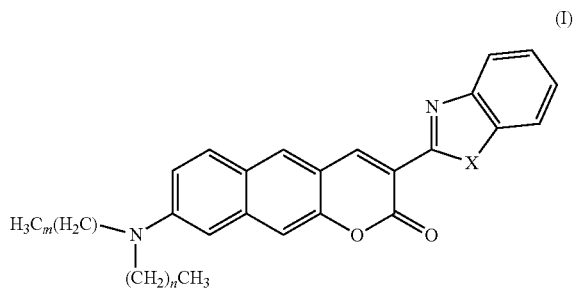

wherein
m represents an integer of 0 to 5;
n represents an integer of 0 to 5;
X is selected from the group consisting of a sulfur atom, an oxygen atom, and a group represented by NR;
R is a hydrogen atom or a group represented by —(CH$_2$)$_y$CH$_3$; and
y represents an integer of 0 to 5; and
detecting a fluorescence signal of the compound to detect the lipid droplet.

2. The detection method according to claim 1, wherein m and n are 1.

3. The detection method according to claim 1, wherein y is 0.

4. The detection method according to claim 1, for detection of a lipid droplet(s) in a biological sample.

5. The detection method according to claim 4, wherein the biological sample is a cell or a tissue.

6. The detection method according to claim 1, for detection of a lipid droplet(s) in a biological individual.

7. The detection method according to claim 1, wherein a solution containing: the compound; and a solubilizer; is administered to a biological sample or a biological individual.

8. The detection method according to claim 7, wherein the solubilizer is albumin.

9. A compound of Formula (I)':

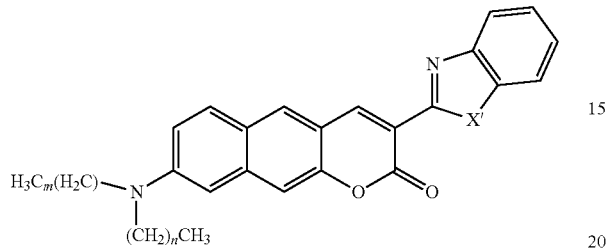

wherein
   m represents an integer of 0 to 5;
   n represents an integer of 0 to 5;
   X' is an oxygen atom.

10. The compound according to claim 9, wherein m and n are 1.

* * * * *